United States Patent [19]

Magiera et al.

[11] Patent Number: 5,893,176
[45] Date of Patent: Apr. 13, 1999

[54] FEMALE URINE DEVICE

[75] Inventors: David L. Magiera, Brooklyn Center; Richard A. Lindell, New Hope, both of Minn.

[73] Assignee: Rainbow Medical, Minneapolis, Minn.

[21] Appl. No.: 08/855,346

[22] Filed: May 13, 1997

[51] Int. Cl.$^6$ .................................................. A47K 11/12
[52] U.S. Cl. ............................ 4/144.4; 4/144.3; 604/329
[58] Field of Search .......................... 4/144.1–144.4; 604/327–331

[56] References Cited

U.S. PATENT DOCUMENTS

| | | | |
|---|---|---|---|
| 1,510,973 | 10/1924 | Behan | 4/144.4 |
| 3,963,020 | 6/1976 | Hall . | |
| 3,964,111 | 6/1976 | Packer | 4/144.4 |
| 3,995,329 | 12/1976 | Williams | 4/144.3 |
| 4,023,216 | 5/1977 | Li . | |
| 4,496,355 | 1/1985 | Hall et al. . | |
| 4,690,677 | 9/1987 | Erb . | |
| 4,815,151 | 3/1989 | Ball | 4/144.1 |
| 4,846,817 | 7/1989 | Mohr et al. . | |
| 4,936,838 | 6/1990 | Cross et al. . | |
| 5,091,998 | 3/1992 | Irazabal | 4/144.4 |
| 5,267,988 | 12/1993 | Farkas . | |

*Primary Examiner*—Charles R. Eloshway
*Attorney, Agent, or Firm*—Patterson & Keough, P.A.

[57] ABSTRACT

A female urine device to direct the discharge of urine while standing. The female urine device incorporates an inner sealing ring, an outer sealing ring and a funnel. The inner sealing ring is adapted to surround and sealingly engage the exterior of the labia minora. The outer sealing ring lies adjacent the inner sealing ring and is adapted to surround and sealingly engage the exterior of the labia majora. The funnel is located below the inner and outer sealing rings and it is adapted to direct the discharge of urine.

15 Claims, 2 Drawing Sheets

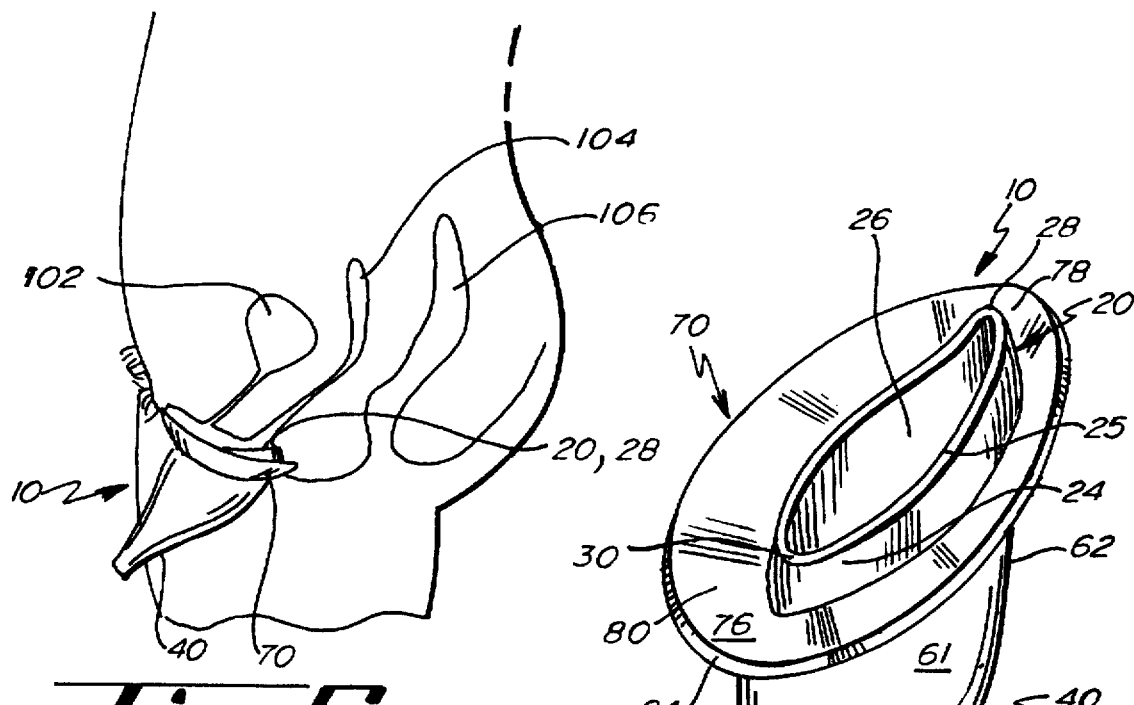
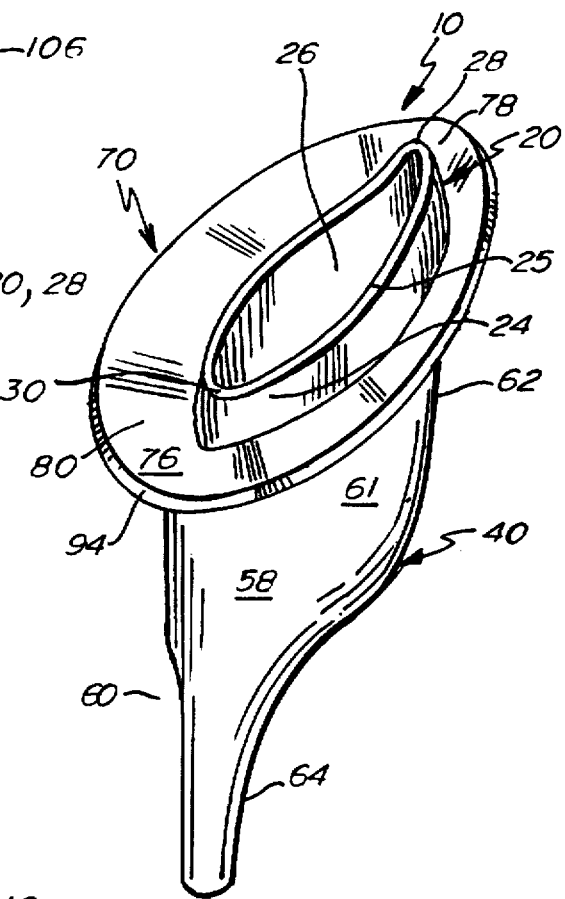
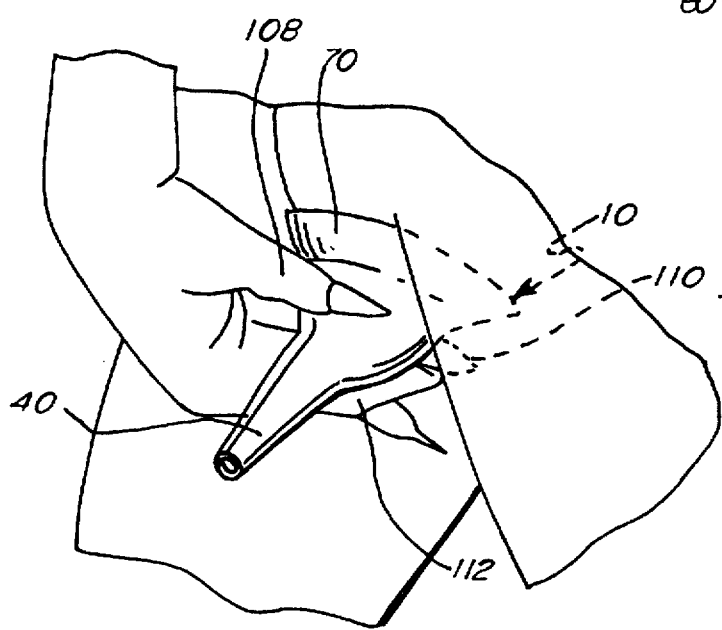

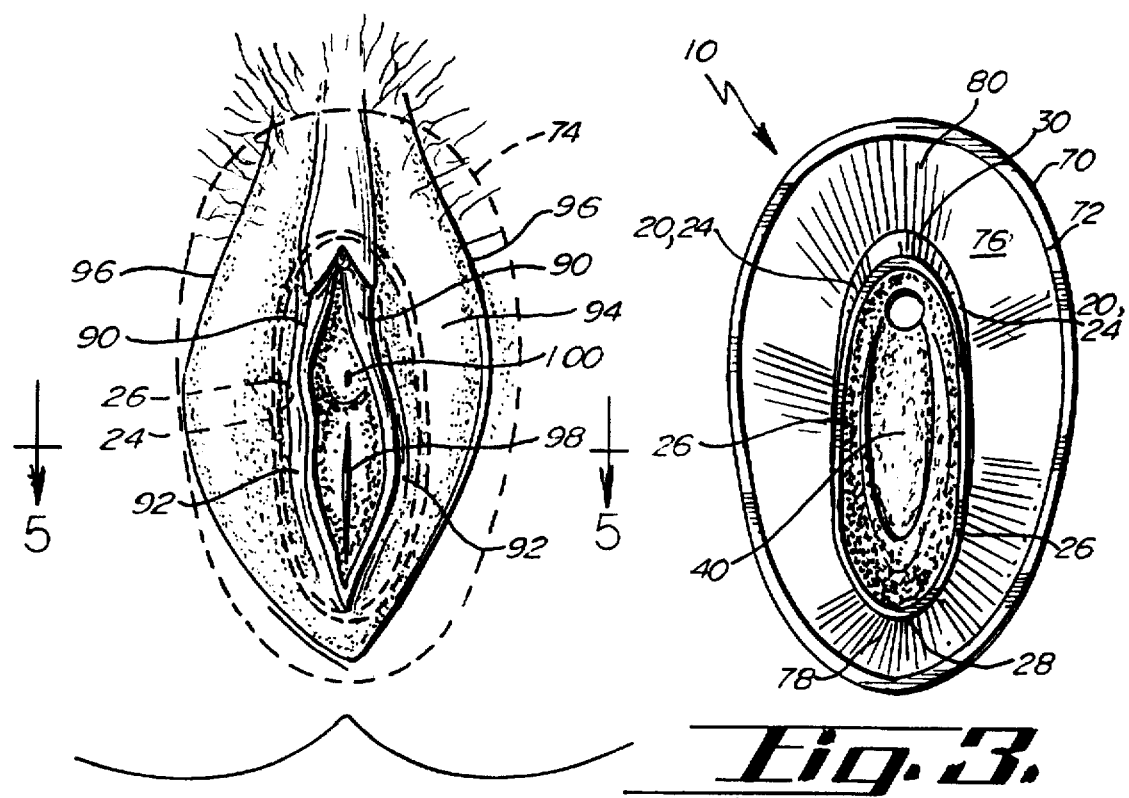
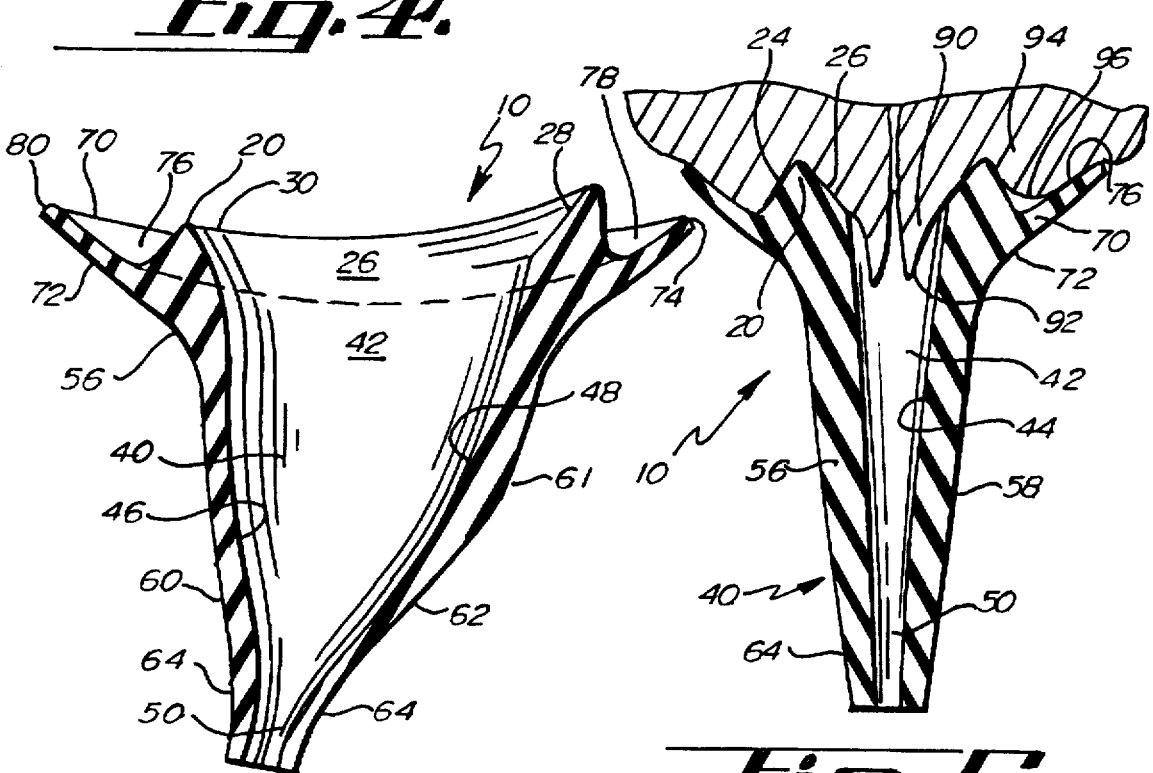

FEMALE URINE DEVICE

BACKGROUND

This invention relates to resolving female sanitary concerns and more particularly to a female urine device for directing urine while standing.

Most women on an everyday basis are faced with the necessity of having to use a public restroom, whether it be on an airplane, at a store or at the workplace. The layout of the female body, along with the clothing that a woman wears, generally dictates that a woman must sit while urinating. However, sitting on a public toilet seat is, more often than not, less than desirable. The public toilet seat may contain visible signs of dirt and urine, and even if the toilet seat appears clean there is always a concern that there may be invisible germs lurking atop the seat waiting to create disease. As a result, women are forced into what may be termed "toilet gymnastics"—attempting to balance oneself over a toilet seat to avoid all contact with the seat.

Moreover, women often find themselves in situations where there are only toilet facilities for men or in situations where there are no toilet facilities at all, e.g. camping in the wilderness. Once again, a woman is faced with performing an awkward balancing act and the possibility of urine wetted or stained clothing.

U.S. Pat. No. 4,023,216 to Li discloses a urinal device that may be used to urinate while standing. However, the design of the Li patent basically discloses a large trough to collect and direct urine. The device does not include any means which will help to position it in the proper manner and further provides no true sealing surface around the labia minora to prevent urine leakage. U.S. Pat. No. 3,963,020 to Hall describes a urinal for human females. This is actually a urine collection device that is meant to be uncomfortably inserted into the vagina and positioned with a hook inserted into the anus. Once again, there is no true sealing surface around the labia minora.

In light of the above, there is a need for a female urine device that will allow a woman to urinate while standing, that will provide for simple and easy positioning of the device, that will be comfortable to the female body, and will provide a seal around the labia minora thereby preventing urine leakage.

SUMMARY

A female urine device to direct the discharge of urine while standing. The female urine device incorporates an inner sealing ring, an outer sealing ring and a funnel. The inner sealing ring is adapted to surround and sealingly engage the exterior of the labia minora. The outer sealing ring lies adjacent the inner sealing ring and is adapted to surround and sealingly engage the exterior of the labia majora. The funnel is located below the inner and outer sealing rings and it is adapted to direct the discharge of urine.

It is an object and advantage of this invention to provide a female urine device that will allow a female to urinate while standing thereby eliminating the need for "toilet gymnastics."

Another object and advantage of this invention is to provide a female urine device that will sealingly engage the labia minora to prevent urine leakage and to provide a funnel portion that will easily direct the flow urine without causing splashing of the urine as it leaves the funnel or without causing backup of the urine that might cause overflow and urine leakage.

Still another object and advantage of this invention is to provide a female urine device that is essentially self positioning, thereby preventing slipping of the device and possible urine leakage.

Yet another object and advantage of this invention is to provide a female urine device that may be applied to the body with the use of only two fingers.

Yet another object and advantage of the present invention is to provide a female urine device that incorporates a second sealing surface that surrounds the labia majora and provides a second layer of protection against urine leakage.

Yet another object and advantage of the present invention is to provide a female urine device that is uniquely similar to the female human from thereby preventing any discomfort or irritation during use.

Yet another object and advantage of the present invention is to provide a female urine device that need not be inserted into any bodily orifices such as the anus, vagina or urethra.

DRAWINGS

These and other features, aspects, and advantages of the present invention will become better understood with regard to the following description, appended claims, and accompanying drawings, where:

FIG. 1 is a perspective view of the female urine device;

FIG. 2 is a side section view of the female urine device;

FIG. 3 is a top view of the female urine device;

FIG. 4 is a view of the female organs of generation, the dashed lines show placement of the female urine device about the labia minora and labia majora;

FIG. 5 is a cross-sectional view taken along line 5—5 of FIG. 4;

FIG. 6 is aside view showing placement of the female urine device on the female body relative to the internal organs; and FIG. 7 is a perspective view showing how the female urine device may be applied to the body with only two fingers.

DETAILED DESCRIPTION

Referring to FIGS. 1, 2 and 3, the female urine device 10 generally comprises an inner sealing ring 20 directed toward a funnel 40 and a outer sealing ring 70 that surrounds the inner sealing ring 20.

The inner sealing ring 20 incorporates two outer walls 24 and two inner walls 26. The outer walls 24 are substantially vertical and extend upward from the outer sealing ring 70 to the perimeter 25 of the inner sealing ring 20. Extending downward from the perimeter 25 toward the funnel 40, are the inner walls 26. The starting point and ending point of the inner walls 26 are defined by a rear extending peak 28 and a front cap portion 30 of the inner sealing ring 20. The inner walls 26 begin with a pronounced taper at the rear extending peak 28 blending to a substantially vertical state at the front cap portion 30. The taper of the inner walls 26 is designed to encompass the female human form. Specifically, the inner walls 26 surround and are conformed to the exterior 92 of the labia minora 90; the pronounced taper of the inner walls 26 surrounds the rearmost portion of the labia minora where the labia minora are quite thin or of little mass (near the opening of the vagina) while the substantially vertical portion of the inner walls allows for the space to surround the larger or more massive front most portion of the labia minora (the point at which the labia minora join or meet).

The inner walls 26 of the inner sealing ring 20 blend smoothly into an inner funnel portion 42 of the funnel 40. The inner funnel portion 42 comprises two side walls 44, a front wall 46, a rear wall 48 and an outlet channel 50. As shown in FIG. 5, the side walls 44 are substantially planar and extend between the inner walls 26 of the inner sealing ring 20 and the outlet channel 50. The side walls 44 smoothly and curvedly blend into the front wall 46. The front wall 46 is substantially vertical with only a slight taper as the front wall extends between the front cap portion 30 of the inner sealing ring and the outlet channel 50. The side walls 44 also blend smoothly and curvedly together to form the rear wall 48. The rear wall 48 tapers significantly as it extends from the inner wall 26, at the rear extending peak 28, to the outlet channel 50. The significant tapering of the rear wall 48 provides the inner funnel portion 42 with its overall elliptical conical shape or ovoid conical shape. All of the walls 44, 46, 48 blend smoothly into the substantially circular outlet channel 50. The outlet channel 50 is provided with an orifice having a diameter in the 4 mm to 5.5 mm range, the preferred diameter at approximately 5 mm.

An outer funnel portion 56 surrounds the inner funnel portion 42. The outer funnel portion 56 incorporates two side walls 58, a front wall 60, a rear wall 62 and an outer channel portion 64. The two side walls 58 are substantially planar and taper slightly outward as they extend between the outer channel portion 64 and the outer sealing ring 70, see FIG. 5. The side walls 58 blend smoothly into the front wall 60 that is substantially vertical as it extends between the outer channel portion 64 and the outer sealing ring 70. The side walls 58 also blend smoothly into the rear wall 62. The rear wall 62 tapers substantially as it extends between the outer channel portion 64 and the outer sealing ring 70. The rear wall 62 is provided with an outward bulge 61.

The walls, 58, 60, 62 of the outer funnel portion 56 smoothly blend into the outer sealing ring 70. The outer sealing ring 70 comprises a flared outer surface 72, a perimeter 74 and a flared inner surface 76. The flared outer surface 72 tapers outward and upward from the outer funnel portion 56 to the outer sealing ring perimeter 74. From the perimeter 74, the flared inner surface 76 of the outer sealing ring 70 tapers downward to meet and join with the outer walls 26 of the inner sealing ring 20. Note that width of the outer sealing ring 70 varies from the rear 78 of the sealing ring 70 to the front 80 of the sealing ring 70. The rear 78 of the outer sealing ring 70 is of a narrower width to accommodate easy placement between the legs. Further, the outer sealing ring 70 is designed to encompass the female human form. Specifically, the flared inner surface 76 surrounds and is conformed to the exterior 96 of the labia majora 94. The narrow width at the rear 78 of the flared inner surface 78 accommodates the narrowness of the labia majora 94 at that point. However, as the labia majora 94 increase in mass and tissue toward the front of the body, the width of the flared inner surface 76 also increases.

The female urine device 10 is appropriately injection molded from various materials that will provide softness and flexibility to the device 20 so as to avoid irritation to the body. These materials can include silicone, thermal rubber or "SANIPRENE," a thermo-plastic rubber. The durometer reading of the material used should be in the range of 40 mm–70 mm, with a preferred durometer reading of 50 mm. A reading under 40 mm will result in a material that is too difficult to cast while a reading over 70 mm will result in a product that is too hard and harsh for the user. Note that the overall size of the female urine device is generally small enough to fit discreetly in the average woman's hand.

The female urine device 10 may be applied to the body using only two fingers, as shown in FIG. 7. The thumb 108 is placed against the front wall 60 of the outer funnel portion 56 proximate the flared outer surface 72 of the outer sealing ring 70. Meanwhile the middle finger 110 is placed on the rear wall 62 of the outer funnel portion 56 just above the wall bulge 61 and just below the flared outer surface 72 of the outer sealing ring 70. Note that the wall bulge 61 provides a mass for the middle finger 110 to press against when pressing the device 10 to the body; the wall bulge prevents slipping of the middle finger 110 and as well, slipping of the device 10. The index finger 112 may simply rest gently against the wall bulge 61 if desired. With the two fingers 108, 110 in place the female urine device 10 is pressed against the body. To ease placement of the device 10 and insure a good seal it is helpful to have the hand that is not holding the female urine device 10 slightly spread apart the labia majora 90.

As the female urine device is pressed to the body, it tends to self-position itself—as the device 10 is pushed or pressed, it slides into the most comfortable position for user. The unique design of the device 10 helps to ensure this effect. Referring to FIGS. 4, 5 and 6, the rear extending peak 28 generally positions directly behind the labia minora 90 and the opening of the vagina 98. The peak 28 is pressed tight against the body and prevents the slipping and sliding of the device 10 specifically, the peak 28 will tend to catch on the labia minora 90 thereby preventing forward movement of the device 10. The inner walls 26 then generally encompass the labia minora 90 and form a snug seal against them when the device 10 is pressed to the body. The front cap portion 30 generally contacts the body just before the labia minora 90 and serves to complete the seal of the inner sealing ring 20 around the labia minora 90. As such, urine is directed down through the inner sealing ring 20, through the inner funnel portion 42 and out the orifice 52. As described earlier, the diameter of the orifice 52 should be in the range of 4 mm to 5.5 mm; a smaller diameter will cause backup of the urine and possible leakage while a larger diameter may cause splashing of the urine as it exits the orifice 52.

As extra leakage protection, the outer sealing ring 70 sealingly engages the labia majora 94. When the female urine device 10 is pressed to the body the flared inner surface 76 of the outer sealing ring 70 cradles the labia majora 94 and seals snugly about the exterior 96 of the labia majora 94, see FIGS. 4, 5 and 6.

Note that every woman's body is different thus, placement of the device 10 as shown in FIGS. 4, 5 and 6 is merely an illustrative example of how the female urine device may fit one woman. In other women slight variations in fit and placement may occur. For instance, the inner sealing ring 20 and the outer sealing ring 70 may fully or only partially surround the labia minora 90 and labia majora 94 respectively, depending on the labia size. However, even though fit and placement may differ slightly from woman to woman, the overall effect of the female urine device 10 is not diminished. The device 10 is still able to accomplish the feat of sealingly engaging the labia minora 90 and labia majora 94 so as to prevent urine leakage and to direct urine flow.

The female urine device 10 is designed to be non-invasive and comfortable to the user, no restriction of the urine flow occurs. Specifically, as shown in FIGS. 4 and 6, the female urine device does not enter the opening of the vagina 98, the opening of the urethra 100 and does not come in contact at all with the area of the anus/rectum 106. As such, no interference with the operation of the bladder 102 or uterus 104 occurs.

The female urine device may be used on any occasion when urination while standing is desirable, e.g. when there is an unavailability of bathroom facilities or when only uncleanly facilities are available.

The present invention may be embodied in other specific forms without departing from the spirit of the essential attributes thereof; therefore, the illustrated embodiment should be considered in all respects as illustrative and not restrictive, reference being made to the appended claims rather than to the foregoing description to indicate the scope of the invention.

What is claimed:

1. A female urine device to direct the discharge of urine while standing, comprising:
   (a) an inner sealing ring adapted to surround and sealingly engage the exterior of the labia minora, said inner sealing ring for substantially containing the discharge of urine;
   (b) an outer sealing ring adjacent said inner sealing ring such that a cup-shaped void exists between said outer sealing ring and said inner sealing ring wherein said cup-shaped void substantially surrounds the periphery of said inner sealing ring and, wherein said outer sealing ring is adapted to surround and sealingly engage the exterior of the labia majora; and
   (c) a funnel located below said inner sealing ring and said outer sealing ring, said funnel adapted to direct the discharge of urine contained by said inner sealing ring, wherein said funnel has an outer funnel portion having a rear wall and a front wall, said rear wall extending from said outer sealing ring to an outlet orifice, said rear wall having an outward extending bulge and a first concave, finger placement portion above said outward extending bulge, said front wall extending from said outer sealing ring to said outlet orifice, said front wall including a second, concave finger placement portion proximate said outer sealing ring.

2. The female urine device of claim 1, wherein said inner sealing ring comprises an inner wall to surround and sealingly engage said exterior of the labia minora.

3. The female urine device of claim 1, wherein said inner sealing ring comprises a rear extending peak.

4. The female urine device of claim 3, wherein said rear extending peak is adapted to contact the female body behind the opening of the vagina and behind the labia minora, said rear extending peak adapted to prevent sliding of said device.

5. The female urine device of claim 1, wherein said outer sealing ring comprises a flared inner surface, said flared inner surface adapted to surround and engage the exterior of the labia majora.

6. The female urine device of claim 5, wherein the width of said flared inner surface is varied to accommodate the varied width of the labia majora.

7. The female urine device of claim 1, wherein said female urine device is applied to the body using only two fingers.

8. The female urine device of claim 1, wherein said outlet orifice has a diameter in the range of 4 mm to 5.5 mm.

9. A female urine device to direct the discharge of urine while standing without being invasive to the orifices or openings of the female human body, comprising:
   (a) an inner sealing ring having a tapered inner wall, said tapered inner wall adapted to surround and sealingly engage the exterior of the labia minora, said inner sealing ring for substantially containing the discharge of urine;
   (b) an outer sealing ring adjacent said inner sealing ring such that a cup-shaped void exists between said outer sealing ring and said inner sealing ring, wherein said cup-shaped void substantially surrounds the periphery of said inner sealing ring and, wherein said outer sealing ring has a flared inner surface, said flared inner surface adapted to surround and sealingly engage the exterior of the labia majora; and
   (c) a funnel, said funnel located below said inner sealing ring and said outer sealing ring, said funnel adapted to direct the discharge of urine contained by said inner sealing ring wherein said funnel has an outer funnel portion having a rear wall and a front wall, said rear wall extending from said outer sealing ring to an outlet orifice, said rear wall having an outward extending bulge and a first concave, finger placement portion above said outward extending bulge, said front wall extending from said outer sealing ring to said outlet orifice, said front wall including a second, concave finger placement portion proximate said outer sealing ring.

10. The female urine device of claim 9, wherein said inner sealing ring further comprises a rear extending peak.

11. The female urine device of claim 10, wherein said rear extending peak is adapted to contact the female body behind the opening of the vagina and behind the labia minora, said rear extending peak adapted to prevent sliding of said device.

12. The female urine device of claim 9, wherein the width of said flared inner surface is varied to accommodate the varied width of the labia majora.

13. The female urine device of claim 9, wherein said female urine device applied to the body using only two fingers.

14. The female urine device of claim 9, wherein said outlet orifice is sized to prevent the backup of urine within said funnel and to prevent splashing of urine as urine discharges from said funnel.

15. The female urine device of claim 14, wherein said outlet orifice has a diameter in the range of 4 mm to 5.5 mm.

* * * * *

UNITED STATES PATENT AND TRADEMARK OFFICE
CERTIFICATE OF CORRECTION

PATENT NO. : 5,893,176
DATED : April 13, 1999
INVENTOR(S) : David L. Magiera, Richard A. Lindell It is certified that error appears in the above-identified patent and that said Letters Patent is hereby corrected as shown below:

Column 1, line 64, please add the words "of the" between the words "flow" and "urine".

Column 2, line 14, please change the word "from" to the word "form".

Column 2, line 46, please change the second occurrence of the word "a" in the sentence to the word "an".

Column 3, line 35, please omit the "," following the word "walls".

Column 4, line 27, please add a "." following the numeral "10". Please begin a new sentence with the word "Specifically".

Column 4, line 47, please add a "." following the word "different". Please begin a new sentence with the word "Thus".

UNITED STATES PATENT AND TRADEMARK OFFICE
CERTIFICATE OF CORRECTION

PATENT NO. : 5,893,176
DATED : April 13, 1999
INVENTOR(S) : David L. Magiera, Richard A. Lindell It is certified that error appears in the above-identified patent and that said Letters Patent is hereby corrected as shown below:

Column 5, line 21, please add a "," following the word "ring".

Column 6, line 46, please insert the word "is" between the words "device" and "applied".

Signed and Sealed this

Fifth Day of October, 1999

*Attest:*

Q. TODD DICKINSON

*Attesting Officer*     Acting Commissioner of Patents and Trademarks